United States Patent [19]

Dorman

[11] 4,046,723
[45] Sept. 6, 1977

[54] AZIDE BONDING OF A PROTEIN TO A LATEX

[75] Inventor: Linneaus C. Dorman, Midland, Mich.

[73] Assignee: The Dow Chemical Company, Midland, Mich.

[21] Appl. No.: 679,639

[22] Filed: Apr. 22, 1976

[51] Int. Cl.$^2$ ............................................. C08L 89/00
[52] U.S. Cl. .................................. 260/8; 260/112 R; 424/12
[58] Field of Search ............... 260/8, 112 R; 424/12

[56] References Cited

U.S. PATENT DOCUMENTS

| 3,666,733 | 5/1972 | Epton | 260/112 R |
| 3,857,931 | 12/1974 | Hager | 424/12 |
| 3,947,352 | 3/1976 | Cuatrecasas | 210/31 C |
| 3,969,287 | 7/1976 | Jaworek et al. | 260/8 |
| 3,985,617 | 10/1976 | Yugari et al. | 260/112 R |

OTHER PUBLICATIONS

Chem. Absts., vol. 78 (1973): 96019x, "Protein-or Peptide-Polystyrene Latex Compositions", Bonacker.

Primary Examiner—Edward M. Woodberry
Attorney, Agent, or Firm—James W. Ambrosius

[57] ABSTRACT

A method of coupling a latex having a surface carboxylic amide group to a protein by an amide bond for producing a composition useful in immunological testing for antibodies or antigen.

6 Claims, No Drawings

AZIDE BONDING OF A PROTEIN TO A LATEX

BACKGROUND OF THE INVENTION

The antigen-antibody reaction is the basis for all immunological test methods. Special proteins called antibodies are produced by an animal in response to the presence of an antigen, that is a foreign protein, in the body fluids of the animal. This normal body response to a foreign protein has led to the development of a number of techniques which are used to diagnose various human and animal diseases or disorders. Immunological test methods have also been used to detect pregnancy. In vitro tests for the presence of a suspected antigen or antibody in a body fluid are carried out by adding the immunological counterpart to a vial of the body fluid, i.e., add antigen if the test is for the presence of antibody or add antibody if the test is for the presence of antigen. If the suspected protein is present the resulting antigen-antibody reaction is generally manifested by precipitation or agglutination of the antigen-antibody complex. As used herein the term body fluid refers to urine, serum, plasma, or the like. In some instances the antigen-antibody complex is slow to form and the particles that are formed are too small to be observed with certainty. In such cases, detectability of the antigen-antibody reaction can be improved by utilizing a carrier. When the antigen or antibody is coated on the surface of a carrier the reaction with the immunological counterpart produces a visible mass or agglutant. The proteinic antigen or antibody may be adsorbed onto the surface of carriers such as erythrocytes, bacterial cells, bentonite, polystyrene latex particles, anionic phenolic resins, or finely divided diazotized amino cellulose. It has been found, however, that chemical binding of the antigen or antibody molecule to the carrier is superior to physical adsorption. U.S. Pat. No. 3,857,931 teaches that proteinic antigens or antibodies can be attached chemically by the formation of an amide bond to a polymer latex carrier having surface carboxyl groups.

The art also teaches that amine-bearing bodies such as peptides and proteins can be chemically attached to polyacrylamide beads by partial hydrazinolysis of surface acrylamide groups followed by a diazotization reaction and the subsequent reaction of the azide formed with a peptide or protein. See U.S. Pat. No. 3,853,987; Inman et al. *Biochemistry* 8, 4074 (1969); Vieth et al. *Chemtech*, p. 47, January (1974); Barber et al., *Process Biochem*, p. 14, August 1970. However, the techniques described are unsatisfactory for use with a latex system which requires special procedures to prevent destabilization of the colloidal system.

SUMMARY OF THE INVENTION

The present invention is directed to a novel process by which proteins can be chemically attached through amide bonds to the surface of latex polymer particles. This is accomplished by a three step reaction sequence. In the first step the surface carboxylic amide groups on the latex polymer particles are hydrazinolyzed at a temperature of about 40° to 60° C to carboxylic hydrazide groups. Carboxylic azide groups are then generated by the careful, limited diazotization of the carboxylic hydrazide groups formed in the first step. This is carried out for example by use of a nitrite, such as sodium nitrite or organic nitrite, in the presence of an acid, preferably a strong mineral acid. Finally chemcial coupling between the protein and the latex takes place by a displacement reaction of the protein's amino groups onto the latex polymer's surface carboxylic azide groups. This called azide coupling. The reaction sequence is illustrated below.

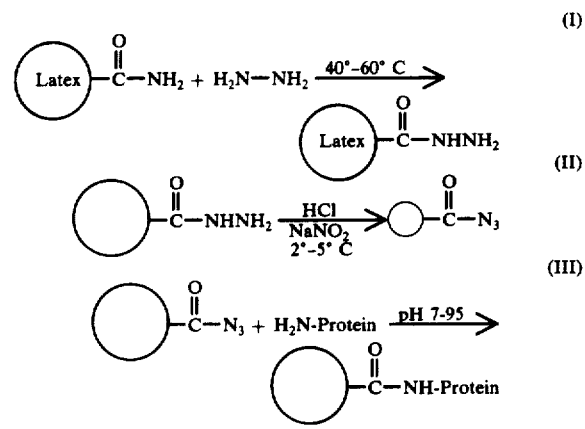

In the final step (III) unchanged azide groups are usually destroyed either by conversion back to amide groups with ammonia or by treatment with another amino body such as glycine.

As used herein the term latex refers to an aqueous colloidal dispersion of a water insoluble polymer. Any latex having surface carboxamido groups attached would be suitable for use in this method. A preferred latex for use in this process is a monodispersed styrene acrylamide latex having about 18.2 percent polymer solids and about 0.233 mequivalents of the carboxamido function per gram of polymer. A monodisperse latex is an aqueous dispersion of colloidal-size particles of the copolymer wherein the standard particles size deviation is less than 2 percent, preferably less than 1 percent. The preparation of a monodispersed styrene acrylamide latex is shown in U.S. patent application Ser. No. 479,957 filed on June 17, 1974.

Monodispersed latexes are preferred because uniformity of size assures an equal statistical distribution of antigen or antibody molecules on the surface of the latex particles. For a given weight of polymer, the total surface area of the latex will increase with a decrease in the size of the particles and vice versa. Thus, in a latex containing a distribution of various particle sizes the smaller particles will have a greater surface area and consequently more total reaction sites than the larger particles. The unequal distribution of antigen or antibody on the latex particles will lead to unequal agglutination of particles and poorly defined diagnostic results.

Another advantage of using uniform latex particles as diagnostic agents is that they are better suited for instrumental analysis. Particles of the same size will flocculate, agglutinate, or settle at the same rate whereas different sized particles will agglutinate at variable rates. Thus an instrumental method based on the absorption or transmission of light through an agglutinating latex suspension will be more accurate, more reproducible, and easier to standardize and read with uniform latex particles than with latexes having varied particle sizes.

DETAILED DESCRIPTION OF THE INVENTION

The method that is the subject of the present invention is applicable to the coupling of any proteinic antigen or antibody having free amino groups at the surface of the molecule to a latex carrier having surface carboxylic amide groups. An example of such a protein is human chorionic gonadotropin, hereinafter called HCG. HCG is a glycoprotein with a molecular weight of about 36,000 produced by the chorionic tissue of the placenta during pregnancy. During pregnancy this hormone governs the production and secretion of progesterone by the corpus luteum. A number of immunological tests have been developed for the detection of HCG in urine and serum. Such test methods are useful in the early detection of pregnancy. HCG is also produced in large quantities by hydatiform moles, choriocarcinomas, and some tumors of the testis. Low levels of HCG have also been found by radioimmunoassay in the sera of patients with various nontrophoblastic neoplasms. Various agglutination techniques have been used to test the presence of HCG.

Agglutination testing for HCG may be performed by either the indirect or the direct technique. In the indirect technique the clinical sample is mixed with HCG antibody at a dilution that will be completely bound by one or more I.U./Ml HCG. After an initial incubation period an indicator system consisting of HCG bound to a particulate carrier (latex or red cells) is added to the mixture. If HCG is present in the clinical sample the HCG antibody will not be available to react with the HCG-carrier complex and there will be no agglutination, thus, absence of agglutination is a positive test for HCG. If, on the other hand, HCG is not present in the clinical sample the HCG antibody will react with the HCG-carrier complex causing agglutination of the indicator system. This is a negative test for HCG in the clinical sample. In the direct technique HCG antibody bound to the carrier reacts directly with the HCG in the clinical sample and there is no need for an intermediate incubation step. Thus, in the direct technique agglutination indicates a positive test for HCG in the clinical sample.

Examples of other proteins which can be coupled to the latex carrier in the same manner as HCG include gamma globulin, albumin, and insulin as well as various protein components isolated from human and animal serum, tissue and cellular extracts, and proteinic components from pathogenic parasites.

The following example illustrates a preferred embodiment of the present invention but is not to be construed as a limitation thereon.

EXAMPLE 1

Azide Bonding Styrene Acrylamide Latex to Human Chorionic Gonadotropin

Hydrazinolysis of Styrene Acrylamide Latex

A 50 ml. quantity of monodispersed styrene acrylamide latex having 18.2 percent polymer solids and 0.233 mequivalents of carboxamido function per gram of polymer was mixed with 5 grams of 95 percent hydrazine. The reaction mass was heated to 48°-52° C with stirring and held under those conditions for 8 hours. The mixture was cooled and transferred to a cellophane dialysis bag where the latex was dialyzed five times against 4 liters of deionized water. The dialysis bath was changed every 24 hours. Tests for the presence of hydrazine were negative following the fifth dialysis. The latex reaction mixture was dialyzed once more against 0.1M sodium chloride. This process yielded 82 grams of hydrazide styrene-acrylamide latex having 12.3 percent solids. Analysis showed the hydrazide functionality of the latex to be 0.099 mequiv/gram polymer.

Larger scale preparations using 250 grams of styrene-acrylamide latex were also carried out using this same procedure. The resulting product was also found to be satisfactory.

The preferred carboxylic hydrazide content in the polymer is 40–45 percent of the total surface functionality. Use of a polymer with a higher hydrazide content may be less stable, and use of a latex with a lower hydrazide content will yield insufficient azide functionality for the desired protein coupling.

Diazatization of the Hydrazide Styrene-Acrylamide Latex

In a siliconized 25 ml round-bottomed flask equipped with a thermometer in the sidearm and containing a Teflon-®coated magnetic stirring bar, 5.0 grams of the hydrazide styrene-acrylamide latex was mixed with 5.0 ml of distilled water. The mixture was stirred and cooled by an external cooling bath. When the mixture reached 9° C, 0.5 ml (0.5 mequiv) of 1N hydrochloric acid was added giving the mixture a pH of less than 1.2. The mixture was further cooled to 2° C at which temperature 0.3 ml (0.03 mequiv) of 0.1M sodium nitrite solution was added dropwise over a period of about 1 minute using a micropipet.

In carrying out the diazotization step a strong, non-oxidizing mineral acid slick as hydrochloric acid is preferred at an equivalency of about 25 times that of the nitrite used. Use of a weak acid prolongs the diazotization time. Fewer acid equivalents will yield a lower acid concentration which will also prolong the diazotization time. Use of a higher acid concentration will require the use of more base to neutralize the mixture prior to the coupling step. This is wasteful and may destabilize the latex The preferred concentration of latex polymer in the diazotization reaction is 5–10 percent. Use of a higher polymer concentration may lead to destabilization of the latex, and the use of lower concentrations will decrease the rate of reaction.

Coupling of Latex Carrier to the Protein

The reaction mixture containing the diazotized latex prepared in Example 2 above was maintained at 2° C. Sodium hydroxide (1N) was added dropwise very slowly to the mixture until the pH was adjusted to about 6. This required that 0.43 ml of sodium hydroxide be added over a period of about 5 minutes. An 8-ml quantity of a cold solution containing 8000 I.U. of HCG in a pH 8.0 phosphate buffer (I = 0.05) and 0.1M NaCl solution was added slowly over a 5 minute period. After addition the pH of the mixture was about 7.2. The reaction mixture was placed in a cold room (5° C) where stirring was continued. After 24 hours a solution of 25 mg (0.33 mmole) of glycine in 1 ml. of water adjusted to a pH of 8.5 with 0.1N sodium hydroxide was added to discharge the unchanged azide groups. After an additional 48 hours in the cold room 19.2 grams of the latex reaction mixture were washed by membrane filtration in a Diaflo® filtration cell (maximum capacity 65 ml) equipped with a white plain Millipore filter (HA 0.45 μ) using pH 8.0 phosphate buffer (I = 0.05) containing 0.1M sodium chloride under a nitrogen pressure of about 3 p.s.i.g. at room temperature. The latex was washed with a total of 130 ml of buffer during 2.7 hours. The latex-HCG product (22.5 grams) was recovered and treated with 22 mg of sodium azide as a preservative.

A range of 2°-5° C is preferred for the coupling reaction. Final washing of the latex to remove unchanged protein may be done at room temperature for convenience but the product should be stored under refrigeration. Higher temperatures may lead to side reactions and loss of carboxylic azide limiting protein coupling. Lower temperatures may lead to freezing of the water in the latex and result in the destruction of the colloidal system.

The preferred time for the coupling reaction to occur is 1-3 days. Longer coupling times may be inconsequential while shorter coupling times may be insufficient for the desired degree of coupling. Coupling is generally carried out at a pH of about 7-9.5.

In carrying out the coupling reaction it is preferred that the proportion of reactants be about 11,000-25,000 I.U. of HCG per gram of polymer. Use of more HCG may be inconsequential while use of less will yield an inferior reaction product.

Using conventional microtiter techniques the latex-HCG preparations showed a detection sensitively of 0.9-1.8 I.U. HCG/ml. Using a plate agglutination technique the detection sensitivity was found to be about 12.5 I.U. HCG/ml.

I claim:

1. A method for coupling a latex having surface carboxylic amide groups to a protein having free amino groups which comprises hydrazinolysing the carboxylic amide group on the latex to a carboxylic hydrazide group by treatment with hydrazine, diazotizing the carboxylic hydrazide group on the latex with a nitrite in the presence of an acid to form a carboxylic azide group, and coupling the carboxylic azide group of the latex with a free amino group on the protein.

2. The method of claim 1 wherein the latex is a monodispersed latex.

3. The method of claim 2 wherein the latex is a monodispersed styrene acrylamide latex.

4. The method of claim 3 wherein the protein is human chorionic gonadotropin.

5. The method of claim 1 wherein the nitrite is sodium nitrite and the acid is a strong non-oxidizing mineral acid.

6. A method for coupling monodispersed styrene acrylamide latex to human chorionic gonadotropin comprising hydrazinolysing the carboxylic amide group on the latex to a carboxylic hydrazide by treatment with hydrazine at a temperature of 40°-60° C, dialyzing the latex for a time sufficient to remove unreacted hydrazine, diazotizing the carboxylic hydrazide group formed on the latex with sodium nitrite and hydrochloric acid, and coupling the human chorionic gonadotropin to the latex at a pH of 7-9.5 at a temperature of 2°-5° C for a period of at least 24 hours.

* * * * *